United States Patent [19]
Kifune et al.

[11] Patent Number: 4,575,519
[45] Date of Patent: Mar. 11, 1986

[54] POROUS CHITIN SHAPED ARTICLE AND PRODUCTION THEREOF

[75] Inventors: Koji Kifune, Nara; Hiroyuki Tanae; Yasuhiko Yamaguchi, both of Kyoto; Kenzo Motosugi, Uji, all of Japan

[73] Assignee: Unitika, Ltd., Hyogo, Japan

[21] Appl. No.: 767,971

[22] Filed: Aug. 21, 1985

[30] Foreign Application Priority Data

Aug. 23, 1984 [JP] Japan ................... 59-176952

[51] Int. Cl.[4] ............... C08D 5/20; C08J 9/00; B32B 9/00
[52] U.S. Cl. ..................... 521/77; 428/403; 428/532; 521/84.1
[58] Field of Search ............. 428/403, 532; 521/77, 521/84.1, 109.1

[56] References Cited
U.S. PATENT DOCUMENTS 4,356,236 10/1982 Koshugi .................. 428/403

Primary Examiner—William J. Van Balen
Attorney, Agent, or Firm—Wenderoth, Lind & Ponack

[57] ABSTRACT

The present invention provides a porous chitin shaped article which has a wet strength of not less than about 1 g/mm$^2$. The shaped article has preferably a porosity of more than 90%.

The present invention also provides a process for preparing the above chitin shaped article, which comprises:
dissolving chitin in a solvent to form a dope, dispersing a water-soluble polymer, which is solid at ambient temperature, in said dope to form a coagulated article, and
removing the water-soluble polymer from said coagulated article by treating with aqueous solution.

5 Claims, No Drawings

POROUS CHITIN SHAPED ARTICLE AND PRODUCTION THEREOF

FIELD OF THE INVENTION

The present invention relates to a novel porous chitin shaped article and the production thereof. More particularly, the present invention relates to a porous chitin shaped article having high mechanical strength, which is useful for a hemostasis material, an adsorption material and the like, and the production thereof.

BACKGROUND OF THE INVENTION

Chitin is an aminopolysuccharide present in exoskeletons of Crustacea, Insecta and the like, in which a repeating unit has one acetylamino group. It is reported that chitin has interesting properties such as high adsorptivity to biological substance, metal and so on, and also wound healing effect.

For utilizing the above mentioned property of chitin, some of porous chitin shaped articles have been proposed in printed documents. However, they did not serve in actual use because of lack of mechanical strength. For example, U.S. Pat. No. 3,988,411 (column 8, line 48) discloses chitin shaped articles including sponge, but it does not disclose concretely the preparation thereof. The use of chitin sponge is also disclosed in "Proceedings of the First chitin/chitosan Conference", National Technical Information Service, U.S. Department of Commerce, Springfield, V.A.22161, (1977), pages 296–305, an article "Application of chitin and chitosan in wound healing acceleration". In the above article, page 300, lines 16–24, it is disclosed that a chitin sponge is prepared by mixing sodium sulfate with a chitin solution formed from a similar process with a cellulose viscose one and then eluting sodium sulfate therefrom. However, there is no description relating to mechanical properties of the chitin sponge.

The inventors of the present invention attempted to apply known processes for a porous cellulose article to the preparation of a chitin article. Examples of known processes include a process which comprises vigorously mixing a viscose solution with a homomixer and then coagulation, and a process which comprises adding a foaming agent to a viscose solution and then foaming it by way of acid or heat, before or during coagulation, to obtain a porous article. It is also known that a process comprises adding a water-soluble compound other than sodium sulfate mentioned above, such as sodium chloride, sodium phosphate and the like, to a viscose solution, coagulation and then removing the water-soluble compound therefrom. In the above attempt by the inventors, the viscose solution was substituted by a chitin solution obtained from a similar process with the viscose one or from dissolving chitin in a solvent. The attempt has failed, because the resultant articles did not have sufficient porosity and were not strong enough to use, especially in wet condition.

SUMMARY OF THE INVENTION

The object of the present invention is to provide a porous chitin shaped article which has excellent strength in wet condition. The chitin shaped article has a wet strength of not less than about 1 g/mm$^2$. The article has preferably a porosity of more than 90%.

The another object of the present invention is to provide a process for preparing the porous chitin shaped article mentioned above, which comprises;
dissolving chitin in a solvent to form a dope, dispersing a water-soluble polymer, which is solid at ambient temperature, in said dope to form a coagulated article, and
removing the water-soluble polymer from said coagulated article by treating with aqueous solution.

DETAILED DESCRIPTION OF THE INVENTION

In the present invention, by "chitin" is meant poly(N-acetyl-D-glucosamine) prepared from treating exoskeletons of Crustacea or Insecta with hydrochloric acid and caustic soda to separate calcium and protein, or a derivative thereof. The derivatives include those deacetylized, etherified, esterified, carboxymethylated, hydroxyethylated or o-ethylated. Representative examples of the derivatives are poly-(N-acetyl-6-o-(2'-hydroxyethyl)-D-glucosamine), poly-(N-acetyl-6-o-ethyl-D-glucosamine) and the like.

A solvent for dissolving chitin in the present invention includes known solvents for chitin, such as a mixture of trichloroacetic acid with a chlorinated hydrocarbon in a weight ratio of 1:2 to 2:1, and an N-methylpyrrolidone solution or a dimethylacetamide solution containing lithium chloride in an amount of 5.5 to 10% by weight.

In the preparation of the porous chitin shaped article of the present invention, chitin is dissolved in the solvent mentioned hereinbefore to obtain a dope. The concentration of chitin in the dope is not more than 20% by weight which has generally been used for conventional shaped articles such as fiber and film. Preferred concentration is within the range of from 0.5 to 5% by weight, because the dope of the present invention turns easily to a high viscosity.

In the present invention, a water-soluble polymer means a natural polymer or synthetic polymer soluble in water, which is solid at ambient temperature. Examples of natural polymers are agar, water-soluble starch, another polysaccharide and protein. Examples of synthetic polymers are polyvinyl alcohol and polycaprolacton. Preferred examples are polyvinyl alcohol and agar. More preferred is a polyvinyl alcohol soluble in cool or hot water and having a degree of hydrolysis of not less than about 60 mole % and a degree of polymerization of about 50 to about 2,000. Most preferred is a polyvinyl alcohol soluble in hot water, for example in water having a temperature of about not less than 60° C., which has a degree of hydrolysis of not less than about 95%. Agar means mucilage present as a cell wall material in red algae such as an agar-agar, a dried one thereof by a freeze-drying process, agarose and agaropectin derived therefrom, and a derivative thereof. These water-soluble polymers are used in the form of powder which may be dispersed in the dope.

The water-soluble polymer is mixed with the chitin dope. The water-soluble polymer is usually presented in the dispersed form, because the water-soluble polymer is not dissolved in the chitin dope. The weight ratio of the chitin dope/the water-soluble polymer is from 1/5 to 5/1. A coagulation agent for the chitin dope containing the water-soluble polymer is alcohols, such as methanol, ethanol, propanol, butanol; ketones, such as acetone; and the like.

According to the present invention, the resultant coagulated dope is treated with an aqueous solution. The aqueous solution may contain a salt, such as sodium chloride in a little amount. The treating temperature and period were selected according to the solubility of the water-soluble polymer to water. The treatment is usually conducted for not less than one hour at a temperature of 80° to 125° C. The chitin shaped article treated with hot water is like sponge in this wet condition. The porous chitin article is usable in this wet condition, and also can be used in dried condition. When used in dried condition, the chitin shaped article may be dried by a conventional drying process, such as an air drying, a vacuum drying or a freeze drying. More preferred is a freeze drying, because the other processes are led to reduce the degree of porosity. The freeze drying can be conducted by freezing the chitin shaped article containing water to about −40° C., followed by drying at about 10° C.

In the present invention, the chitin shaped article can be sheet, block, sphere, football shape, cyrindrical shape and like, which having porosity ($B/A \times 100$; wherein B is a pore volume contained in the porous article having the unit weight, and A is a total volume of the porous article having the unit weight.) of not less than about 90%.

The porous shaped article of the present invention has a wet strength of not less than about 1 $g/mm^2$, preferably not less than 3 $g/mm^2$, more preferably not less than 5 $g/mm^2$. The wet strength is measured by a process comprising dipping the porous article in water at 25° C. for one hour, followed by pulling it off by the aid of a test machine and then reading a value of strength when the article is cut off. The value is usually represented in terms of strength per the unit area (1 $mm^2$), which is converted from a cut area prior to cutting off. Wet strengths less than about 1 $g/mm^2$ are undesirable, because the shape of the article is liable to be broken when an external force such as compression force is applied to the article. For example, when the article has a wet strength of less than about 1 $g/mm^2$ and is led to absorb blood, the shape of the article is easily broken by compression by fingers or other forces.

The chitin shaped article of the present invention has high mechanical strength. It also has high absorbability when it is used in wet condition and it keeps its shape even in such a wet condition. Therefore, the chitin article is very useful as a hemostasis material or adsorption material.

Illustrating the invention are the following examples, which however, are not to be construed as limiting the invention to their details. All parts and percentages in the examples are by weight unless otherwise specified.

EXAMPLES

Example 1

A chitin powder (available from Kyowa Yushi, K.K.) was ground to 100 mesh. The resultant powder was treated with 1N-HCl at 4° C. for one hour and then heated at a temperature of 90° to 100° C. for 3 hours in a 3% NaOH solution to remove calcium and protein containing in the chitin powder, followed by washing several times and drying. The resultant chitin was dissolved in a dimethylacetamide solution containing 8% by weight of calcium chloride at room temperature to obtain a mixture containing 2% by weight of chitin. The mixture was filtrated under pressure with 1480 mesh stainless net and defoamed with stirring under a vacuumed condition to obtain a chitin dope. To 100 g of the chitin dope, 50 g of polyvinyl alcohol (degree of polymerization: 170, degree of hydrolysis: not less than 95 mole %, which is available from Unitika Chemical Co., Ltd. as POVAL UF-170GS) was added and stirred for one hour in a beaker equipped with a stirring blade to obtain a homogeneous dispersion. The dispersion was casted on a glass plate in 0.5 cm thickness, which was then dipped in water at about 25° C. to coagulate and wash, thus forming a sheet. The sheet was dipped in large amount of water and treated for 5 hours with boiling water, thus obtaining a porous chitin shaped article in the form of a plate.

The resultant article was frozen at −40° C. and freeze-dried at 10° C. to obtain a dried porous chitin shaped article. The obtained article has the porosity of 99.2% and the wet strength of 5.3 $g/mm^2$, which indicates a high strength in wet condition.

Comparative Example 1

To one hundred gram of the dope obtained in Example 1 was added 50 g of sodium sulfate and mixed, followed by coagulation and heating with hot water as described generally in Example 1 to obtain a sheet. The obtained sheet has the porosity of 55%, which does not indicate porous. It was a sheet that its volume was reduced with removing sodium sulfate. It did not indicate porous even when it was dried by a freeze-dry process.

Example 2

The chitin powder obtained in Example 1 was dissolved in a dimethylacetamide solution containing 8% by weight to obtain a 1% by weight solution. The solution was filtrated and defoamed to obtain a clear chitin dope. One hundred gram of agar powder (which is available from Wako Junyaku Co., Ltd. as KANTENMATSU) was added to 100 g of the chitin dope to form a uniform mixture. This mixture was charged in a pressure tank and transmitted by a gear pump and then extruded from a circle nozzle equipped with a tip point of the tank into methanol to form a cylindrical chitin article. After washing in methanol to remove the solvent, the article was treated in boiling water for 10 hours to obtain a soft article in a wet condition. After freezing at −40° C., the article was freeze-dried at 10° C. to obtain a porous chitin shaped article which has the porosity of 99.2%. The wet strength of the porous chitin article was 7.2 $g/mm^2$.

Comparative Example 2

One hundred gram of the chitin obtained in Example 1 was dipped in 300 g of a 40% (w/w) sodium hydroxide solution at 11° to 13° C. for 2 hours and then at 0° to 5° C. for 10 hours to form an alkalized chitin. The obtained alkalized chitin was compressed to three times of the original chitin volume to remove excess of sodium hydroxide and then ground by a mixer. This alkalated chitin was charged in a separating funnel and stood for 10 hours at −20° C. under a vacuum condition. Carbon disulfide of 50% by weight of the original chitin was poured by means of vacuum in the funnel and chitosangelled at 30° C. for 15 hours with stirring occasionally. An aqueous sodium hydroxide which was already cooled to 0° C. was added to the obtained chitin to obtain a solution containing the alkali concentration of 4.5% and the chitin concentration of 5%, which was frozen at −20° C. for 5 hours. The frozen chitin was heated to 0° to 5° C. over 3 hours to form a uniform chitin viscose. To 50 g of this viscose solution, 30 g of sodium sulfate was added and applied to a glass plate in the 0.5 cm thickness to obtain a sheet. After this sheet was dipped in a 5% sulfuric acid solution to coagulate, the sheet was washed by distilled water for 10 hours and then frozen at −40° C., followed by freeze-drying to obtain a sheet. This sheet lost its shape in wet condition and has the wet strength of 0.1 g/mm².

Example 3 to 5 and Comparative Example 3 to 5

The mixture of the dope and the agar powder used in Example 2 was filled up in 2 cm long×3 cm broad×1 cm thickness containers and coagulated with water. Then the containers were treated with boiling water for 10 hours to obtain 6 porous chitin articles in wet condition. The size of the article was about 2 cm long×about 3 cm broad×about 1 cm thickness and the articles have the porosity of 99.2%. These article were treated with a 0.1N aqueous hydrochloric acid for various periods within the range of 0.2 to 2 hours to obtain 6 samples as shown in Table 1, which have various wet strengths. After washing the samples, they were placed at a level in wet condition and stainless plates (3 cm long×4 cm broad×0.5 mm thickness) were put on the surface of the samples. In addition, 100 g balance weights were put on the stainless plates and the samples were maintained for 10 minutes. The stainless plates and weights were then removed and the samples were dipped again in water. Their thicknesses were measured and showen in Table 1.

TABLE 1

|  | Treating period by acid (hr) | Wet strength (g/mm²) | Thickness after compression (mm) |
| --- | --- | --- | --- |
| Example 3 | — | 7.2 | 9.6 |
| Example 4 | 0.2 | 4.2 | 9.3 |
| Example 5 | 0.5 | 1.8 | 9.1 |
| Comparative example 3 | 0.75 | 0.81 | 5.4 |
| Comparative example 4 | 1.0 | 0.62 | 4.6 |
| Comparative example 5 | 2.0 | 0.29 | 3.7 |

In the samples of Examples 3 to 5, their thicknesses were recovered to the same level as was prior to addition of weights, after removing weights in wet condition, while, in Comparative Examples 3 to 5, the articles were substantially broken and could not recover as before any more.

What is claimed is:

1. A porous chitin shaped article characterized by having a wet strength of not less than about 1 g/mm².

2. The chitin shaped article of claim 1 in which the article has a porosity of not less than 90%.

3. A process for preparing a porous chitin shaped article having a wet strength of not less than about 1 g/mm², which comprises;
   dissolving chitin in a solvent to form a dope, dispersing a water-soluble polymer, which is solid at ambient temperature, in said dope to form a coagulated article, and
   removing the water-soluble polymer from said coagulated article by treating with aqueous solution.

4. The process of claim 3 wherein the water-soluble polymer is polyvinyl alcohol.

5. The process of claim 3 wherein the water-soluble polymer is agar.

* * * * *